(12) United States Patent
Ideker et al.

(10) Patent No.: US 7,734,344 B2
(45) Date of Patent: Jun. 8, 2010

(54) METHODS, SYSTEMS AND COMPUTER PROGRAM PRODUCTS TO INHIBIT VENTRICULAR FIBRILLATION DURING CARDIOPULMONARY RESUSCITATION

(75) Inventors: Raymond E. Ideker, Birmingham, AL (US); Gregory P. Walcott, Wilsonville, AL (US)

(73) Assignee: UAB Research Foundation, Birmingham, AL (US)

( * ) Notice: Subject to any disclaimer, the term of this patent is extended or adjusted under 35 U.S.C. 154(b) by 1539 days.

(21) Appl. No.: 10/727,123

(22) Filed: Dec. 2, 2003

(65) Prior Publication Data
US 2005/0119706 A1 Jun. 2, 2005

(51) Int. Cl.
*A61N 1/39* (2006.01)
(52) U.S. Cl. .............................. 607/5; 607/3
(58) Field of Classification Search ............. 607/3, 607/5; 601/41, 43, 44
See application file for complete search history.

(56) References Cited

U.S. PATENT DOCUMENTS

| | | | |
|---|---|---|---|
| 2,071,215 A | 2/1937 | Petersen | |
| 3,219,031 A | 11/1965 | Rentsch, Jr. | |
| 3,455,298 A | 7/1969 | Anstadt | |
| 3,461,861 A | 8/1969 | Barkalow et al. | |
| 3,509,899 A | 5/1970 | Hewson | |
| 3,613,672 A | 10/1971 | Schiff | 128/24.5 |
| 3,825,015 A | 7/1974 | Berkovits | 128/404 |
| 3,896,797 A | 7/1975 | Bucur | |
| 3,995,623 A | 12/1976 | Blake et al. | 128/2.06 E |
| 4,048,990 A | 9/1977 | Goetz | 128/64 |
| 4,192,293 A | 3/1980 | Asrican | 128/1 D |
| 4,273,114 A | 6/1981 | Barkalow et al. | 128/53 |
| 4,355,646 A | 10/1982 | Kallok et al. | 128/786 |
| 4,365,639 A | 12/1982 | Goldreyer | 128/786 |
| 4,397,306 A | 8/1983 | Weisfeldt et al. | |
| 4,424,806 A | 1/1984 | Newman et al. | |
| 4,444,195 A | 4/1984 | Gold | 128/642 |
| 4,499,907 A | 2/1985 | Kallok et al. | 128/786 |
| 4,536,893 A | 8/1985 | Parravicini | 623/3 |
| 4,559,946 A | 12/1985 | Mower | 128/419 D |
| 4,567,901 A | 2/1986 | Harris | 128/786 |
| 4,637,397 A | 1/1987 | Jones et al. | 128/419 D |
| 4,643,201 A | 2/1987 | Stokes | 128/786 |
| 4,690,134 A | 9/1987 | Snyders | 128/64 |

(Continued)

FOREIGN PATENT DOCUMENTS

EP 0095726 B1 2/1988

(Continued)

OTHER PUBLICATIONS

Link, Mark S. Commotio cordis: sudden death due to chest wall impact in sports. Heart. Feb. 1999;81(2):109-10.*

(Continued)

*Primary Examiner*—Mark W Bockelman
*Assistant Examiner*—Eric D Bertram
(74) *Attorney, Agent, or Firm*—Myers Bigel Sibley & SAjovec (57) ABSTRACT

Methods, systems and computer program products determine and identify a favorable time to deliver cardiac compression to a subject to avoid a vulnerable period of a spontaneous intrinsic cardiac cycle.

32 Claims, 6 Drawing Sheets

U.S. PATENT DOCUMENTS

| | | | |
|---|---|---|---|
| 4,693,253 A | 9/1987 | Adams | 128/419 D |
| 4,708,145 A | 11/1987 | Tacker, Jr. et al. | 128/419 D |
| 4,731,076 A | 3/1988 | Noon et al. | 623/3 |
| 4,800,883 A | 1/1989 | Winstrom | 128/419 D |
| 4,850,357 A | 7/1989 | Bach, Jr. | 128/419 D |
| 4,901,725 A | 2/1990 | Nappholz et al. | 128/419 |
| 4,928,674 A | 5/1990 | Halperin et al. | |
| 4,928,688 A | 5/1990 | Mower | 128/419 |
| 5,107,834 A | 4/1992 | Ideker et al. | 128/419 D |
| 5,165,403 A | 11/1992 | Mehra | 128/419 |
| 5,169,381 A | 12/1992 | Snyders | 600/16 |
| 5,184,616 A | 2/1993 | Weiss | 128/419 |
| 5,201,808 A | 4/1993 | Steinhaus et al. | 128/419 |
| 5,209,229 A | 5/1993 | Gilli | 128/419 |
| 5,224,476 A | 7/1993 | Ideker et al. | 128/419 D |
| 5,230,337 A | 7/1993 | Dahl et al. | 607/5 |
| 5,235,977 A | 8/1993 | Hirschberg et al. | 607/5 |
| 5,235,978 A | 8/1993 | Hirschberg et al. | 607/5 |
| 5,239,988 A | 8/1993 | Swanson et al. | 128/28 |
| 5,251,624 A | 10/1993 | Bocek et al. | 607/6 |
| 5,256,132 A | 10/1993 | Snyders | 600/16 |
| 5,267,559 A | 12/1993 | Jin et al. | 128/419 D |
| 5,269,298 A | 12/1993 | Adams et al. | 128/419 D |
| 5,269,319 A | 12/1993 | Schulte et al. | 128/786 |
| 5,282,836 A | 2/1994 | Kreyenhagen et al. | 607/4 |
| 5,292,338 A | 3/1994 | Bardy | 607/5 |
| 5,295,481 A | 3/1994 | Geehan | 601/41 |
| 5,303,702 A | 4/1994 | Bonnet et al. | 607/20 |
| 5,304,139 A | 4/1994 | Adams et al. | 607/122 |
| 5,304,218 A | 4/1994 | Alferness | 607/122 |
| 5,312,444 A | 5/1994 | Bocek et al. | 607/5 |
| 5,313,953 A | 5/1994 | Yomtov et al. | 600/508 |
| 5,314,430 A | 5/1994 | Bardy | 607/5 |
| 5,324,309 A | 6/1994 | Kallok | 607/5 |
| 5,331,966 A | 7/1994 | Bennett et al. | 128/696 |
| 5,332,400 A | 7/1994 | Alferness | 607/5 |
| 5,344,430 A | 9/1994 | Berg et al. | 607/8 |
| 5,348,021 A | 9/1994 | Adams et al. | 128/708 |
| 5,350,402 A | 9/1994 | Infinger et al. | 607/5 |
| 5,366,485 A | 11/1994 | Kroll et al. | 607/5 |
| 5,366,486 A | 11/1994 | Zipes et al. | 607/5 |
| 5,385,528 A | 1/1995 | Wilk | 600/18 |
| 5,387,233 A | 2/1995 | Alferness et al. | 607/126 |
| 5,395,373 A | 3/1995 | Ayers | 607/8 |
| 5,403,351 A | 4/1995 | Saksena | 607/4 |
| 5,403,354 A | 4/1995 | Adams et al. | 607/5 |
| 5,405,375 A | 4/1995 | Ayers et al. | 607/122 |
| 5,411,527 A | 5/1995 | Alt | 607/5 |
| 5,423,772 A | 6/1995 | Lurie et al. | 607/282 |
| 5,431,681 A | 7/1995 | Helland | 607/4 |
| 5,431,682 A | 7/1995 | Hedberg | 607/5 |
| 5,431,683 A | 7/1995 | Bowald et al. | 607/5 |
| 5,433,729 A | 7/1995 | Adams et al. | 607/5 |
| 5,433,730 A | 7/1995 | Alt | 607/5 |
| 5,441,519 A | 8/1995 | Sears | 607/5 |
| 5,443,491 A | 8/1995 | Snichelotto | 607/122 |
| 5,447,519 A | 9/1995 | Peterson | 607/5 |
| 5,456,706 A | 10/1995 | Pless et al. | 607/122 |
| 5,464,429 A | 11/1995 | Hedberg et al. | 607/4 |
| 5,464,432 A | 11/1995 | Infinger et al. | 607/5 |
| 5,466,221 A | 11/1995 | Zadini et al. | 604/96 |
| 5,470,348 A | 11/1995 | Neubauer et al. | 607/68 |
| 5,476,498 A | 12/1995 | Ayers | 607/122 |
| 5,476,499 A | 12/1995 | Hirschberg | 607/123 |
| 5,484,391 A | 1/1996 | Buckman, Jr. et al. | 601/135 |
| 5,486,199 A | 1/1996 | Kim et al. | 607/5 |
| 5,487,753 A | 1/1996 | MacCarter et al. | 607/17 |
| 5,489,293 A | 2/1996 | Pless et al. | 607/5 |
| 5,496,345 A | 3/1996 | Kieturakis et al. | 606/192 |
| 5,514,153 A | 5/1996 | Bonutti | 606/190 |
| 5,522,853 A | 6/1996 | Kroll | 607/5 |
| 5,531,764 A | 7/1996 | Adams et al. | 607/5 |
| 5,540,711 A | 7/1996 | Kieturakis et al. | 606/192 |
| 5,554,176 A | 9/1996 | Maddison et al. | 607/9 |
| 5,560,369 A | 10/1996 | McClure et al. | 128/704 |
| 5,571,074 A | 11/1996 | Buckman, Jr. et al. | 601/6 |
| 5,573,517 A | 11/1996 | Bonutti et al. | 604/264 |
| 5,578,064 A | 11/1996 | Prutchi | 607/19 |
| 5,582,580 A | 12/1996 | Buckman, Jr. et al. | 601/41 |
| 5,584,865 A | 12/1996 | Hirschberg et al. | 607/5 |
| 5,593,418 A | 1/1997 | Mollenauer | 606/192 |
| 5,601,581 A | 2/1997 | Fogarty et al. | 606/159 |
| 5,601,589 A | 2/1997 | Fogarty et al. | 606/192 |
| 5,601,590 A | 2/1997 | Bonutti et al. | 606/192 |
| 5,607,443 A | 3/1997 | Kieturakis et al. | 606/192 |
| 5,609,621 A | 3/1997 | Bonner | 607/122 |
| 5,618,287 A | 4/1997 | Fogarty et al. | 606/129 |
| 5,620,471 A | 4/1997 | Duncan | 607/14 |
| 5,624,381 A | 4/1997 | Kieturakis et al. | 600/206 |
| 5,630,789 A | 5/1997 | Schock et al. | 601/41 |
| 5,653,726 A | 8/1997 | Kieturakis et al. | 606/190 |
| 5,667,479 A | 9/1997 | Kieturakis et al. | 600/207 |
| 5,667,520 A | 9/1997 | Bonutti | 606/190 |
| 5,683,364 A | 11/1997 | Zadini et al. | 604/98 |
| 5,683,429 A | 11/1997 | Mehra | 602/14 |
| 5,685,826 A | 11/1997 | Bonutti | 600/204 |
| 5,690,668 A | 11/1997 | Fogarty et al. | 606/192 |
| 5,694,951 A | 12/1997 | Bonutti | 128/898 |
| 5,697,953 A | 12/1997 | Kroll et al. | 607/5 |
| 5,702,416 A | 12/1997 | Kieturakis et al. | 606/193 |
| 5,702,417 A | 12/1997 | Hermann | 606/194 |
| 5,707,390 A | 1/1998 | Bonutti | 606/204 |
| 5,716,325 A | 2/1998 | Bonutti | 600/204 |
| 5,718,718 A | 2/1998 | Kroll et al. | 607/5 |
| 5,730,748 A | 3/1998 | Fogarty et al. | 606/159 |
| 5,730,756 A | 3/1998 | Kieturakis et al. | 606/190 |
| 5,772,613 A * | 6/1998 | Gelfand et al. | 601/41 |
| 5,800,469 A | 9/1998 | Nappholz | 607/18 |
| 5,800,470 A | 9/1998 | Stein et al. | 607/20 |
| 5,861,012 A | 1/1999 | Stroebel | 607/28 |
| 5,978,704 A | 11/1999 | Ideker et al. | 607/123 |
| 5,978,705 A | 11/1999 | KenKnight et al. | 607/5 |
| 5,987,354 A | 11/1999 | Cooper et al. | 607/5 |
| 6,002,962 A | 12/1999 | Huang et al. | 607/5 |
| 6,006,131 A | 12/1999 | Cooper et al. | 607/5 |
| 6,059,750 A | 5/2000 | Fogarty et al. | 604/96 |
| 6,148,230 A | 11/2000 | KenKnight | 600/516 |
| 6,179,793 B1 * | 1/2001 | Rothman et al. | 601/44 |
| 6,198,968 B1 * | 3/2001 | Prutchi et al. | 607/9 |
| 6,200,280 B1 | 3/2001 | Brenneman et al. | 601/41 |
| 6,275,730 B1 | 8/2001 | KenKnight et al. | 607/5 |
| 6,285,907 B1 | 9/2001 | Kramer et al. | 607/9 |
| 6,287,267 B1 | 9/2001 | Brenneman et al. | 601/41 |
| 6,327,500 B1 | 12/2001 | Cooper et al. | 607/5 |
| 6,371,119 B1 | 4/2002 | Zadini et al. | 128/845 |
| 6,374,827 B1 | 4/2002 | Bowden et al. | 128/207.14 |
| 6,388,866 B1 | 5/2002 | Rorvick et al. | 361/503 |
| 6,390,996 B1 * | 5/2002 | Halperin et al. | 601/41 |
| 6,406,444 B2 | 6/2002 | Brenneman et al. | 601/41 |
| 6,503,265 B1 | 1/2003 | Fogarty et al. | 606/192 |
| 2001/0027279 A1 | 10/2001 | Rothman et al. | 601/41 |

FOREIGN PATENT DOCUMENTS

| | | |
|---|---|---|
| EP | 0472 411 A1 | 2/1992 |
| EP | 0509773 A1 | 4/1992 |
| EP | 0554 208 A2 | 8/1993 |
| EP | 0 601 340 A1 | 6/1994 |
| EP | 0804938 A2 | 11/1997 |
| WO | WO96/23546 | 8/1996 |
| WO | WO 97/01373 | 1/1997 |

| | | |
|---|---|---|
| WO | WO99/65561 | 12/1999 |

OTHER PUBLICATIONS

U.S. Appl. No. 10/238,343, filed Sep. 10, 2002, Ideker et al.

Allessie et al., "Regional control of atrial fibrillation by rapid pacing in concious dogs," *Circulation* 1991;84:1689-1697.

Capucci et al., "Capture window in human atrial fibrillation: evidence of an excitable gap," *J Cardiovasc Electrophysiol* 1999;10:319-327.

Cooper et al., "Internal Cardioversion of Atrial Fibrillation in Sheep," Atrial Fibrillation: Mechanisms and Therapeutic Strategies, (1994) pp. 325-332.

Cooper et al., "Internal Cardioversion of Atrial Fibrillation in Sheep," Circulation, vol. 87, No. 5, May 1993, pp. 1673-1685.

Daoud et al. "Response of Type I atrial fibrillation to atrial pacing in humans," Circulation 1996;94:1036-1040.

Feeser et al., "Strength-Duration and Probability of Success Curves for Defibrillation with Biphasic Waveforms," *Circulation*, vol. 82, No. 6, Dec. 1990, pp. 2128-2141.

Garcia-Calvo et al., "The effects of selective stellate ganglion manipulation on ventricular refractoriness and excitability," PACE, 1992;15:1492-1503.

Halperin et al., "A Preliminary Study of Cardiopulmonary Resuscitation by Circumferential Compression of the Chest with Use of a Pneumatic Vest," The New England Journal of Medicine, Sep. 9, 1993, vol. 329:762-768.

Huang et al., "Evolution of the organization of epicardial activation patterns during ventricular fibrillation," J Cardiovasc Electrophysiol, 1998;9:1291-1304.

KenKnight et al., "Regional capture of fibrillating ventricular myocardium: Evidence of an excitable gap," Circ Res 1995;77:849-855.

Kirchhof et al., "Regional entrainment of atrial fibrillation studied by high-resolution mapping in open-chest dogs," Circulation 1993;88:736-749.

Knisley et al., "Line stimulation parallel to myofibers enhances regional uniformity of transmembrane voltage changes in rabbit hearts," Circ Res 1997;81:229-241.

Kroll, Mark W., "A Minimal Model of the Monophasic Defibrillation Pulse," PACE, vol. 16, Apr. 1993, Part I, pp. 769-777.

Lammers, W. J.E.P. et al., *The use of fibrillation cycle length to determine spatial dispersion in electrophysiological properties and to characterize the underlying mechanism of fibrillation*, New Trends in Arrhythmias, vol. II, N.1, Jan.-Mar. 1986, pp. 109-112.

Lewalter et al., "The Low Intensity Treadmill Exercise" Protocol for Appropriate Rate Adaptive Programming of Minute Ventilation Controlled Pacemakers, (Jul. 1995) PACE, 18:1374-1387.

Lok et al.; "Clinical Shock Tolerability and Effect of Different Right Atrial Electrode Locations on Efficacy of Low Energy Human Transvenous Atrial Defibrillation Using an Implantable Lead System", *JACC* 30:5 (1997) 1324-1330.

Lüderitz et al., "Nonpharmacologic Strategies for Treating Atrial Fibrillation," The American Journal of Cardiology, vol. 77, Jan. 25, 1996, pp. 45A-52A.

Neri et al.; "Internal Cardioversion of Chronic Atrial Fibrillation in Patients", *PACE* 20 (1997) 2237-2242.

Opthof et al., "Dispersion of refracteries in canine ventricular myocardium: Effects of sympathetic stimulation," Circ Res 1991;68:1204-1215.

Prof. Dr. med. Eckhard Alt; "Letters to the Editor", (1998) *PACE* 21 633-634.

Province et al., "Effect of pulse train amplitude and waveform on ability to entrain fibrillating rabbit ventricle with epicardial pacing," (1999) PACE, 22:A66 (Abstract).

Qin, Hao et al., "Recurrence Patterns After Failed Defibrillation of Spontaneous Ventricular Fibrillation During Acute Ischemia," Supplement to Journal of the American College of Cardiology, p. 3, Mar. 6, 2002, vol. 39, No. 5 Supplement A.

Qin, Hao et al., "Difibrillation Efficacy for Spontaneous and electrically-Induced Ventricular Fibrillation During Acute Ischemia," Supplement to Circulation Journal of the American Heart Association, #2125, 2000.

Qin, Hao et al., "Impact of Myocardial Ischemia and Reperfusion on Ventricular Defibrillation Patterns, Energy Requirements, and Detection of Recovery," (Circulation 2002;105:2537) Published online before print May 6, 2002, 10.1161/01.CIR.0000016702.86180.F6.

Rogers et al., "A quantitative framework for analyzing epicardial activation patterns during ventricular fibrillation," Ann Biomed Eng 1997; 25:749-760.

Rogers et al., "Recurrent wavefront morphologies: a method for quantifying the complexity of epicardial activation patterns," Ann Biomed Eng 1997; 25:761-768.

Rollins et al., "Macintosh based programmable cardiac stimulatr," J Am Coll Cardiol, 15:261A (1990) Abstract.

Rozenberg et al., "Prehospital use of minimally invasive direct cardiac massage (MIDCM): a pilot study," Resuscitation 50 (2001) 257262.

Vander et al. *"Human Physiology—The Mechanisms of Body Functio,"* Jan. 1985 pp. 230-236.

Wharton et al., "Cardiac potential and potential gradient fields generated by single, combined, and sequential shocks during ventricular defibrillation," Circulation 1992; 85:1510-1523.

Wright et al., "Cardiac Rhythm Management Laboratory: In Vivo Study Protocol, Internal Atrial Defibrillation in Sheep Using Sequential Biphasic Waveforms," CRM Laboratory, University of Alabama—Birmingham Medical Center, Oct. 1995.

PCT International Search Report, International Application No. PCT/US2004/039986 mailed Apr. 18, 2005.

* cited by examiner

METHODS, SYSTEMS AND COMPUTER PROGRAM PRODUCTS TO INHIBIT VENTRICULAR FIBRILLATION DURING CARDIOPULMONARY RESUSCITATION

FIELD OF THE INVENTION

The present invention relates to methods and devices for inhibiting fibrillation.

BACKGROUND OF THE INVENTION

When a subject undergoes cardiopulmonary resuscitation (CPR) for decreased or absent cardiac contraction, arrhythmias (such as ventricular fibrillation) can occur even after initially successful defibrillation or reactivation of the cardiac cycle.

SUMMARY

Certain embodiments of the present invention provide devices, methods and computer program products that can allow cardiac compression to be selectively delivered during cardiopulmonary resuscitation and to be timed to a desired portion of an intrinsic spontaneous cardiac cycle and/or an electrical stimulus event to inhibit arrhythmias and/or improve cardiac function.

Certain embodiments of the present invention are directed toward methods for performing chest compression during cardiopulmonary resuscitation (CPR). The methods include: (a) electrically stimulating a subject's heart during cardiopulmonary resuscitation; and (b) compressing the heart at a selected time proximate to the delivery of the electrical stimulation to avoid compressing the heart during a vulnerable portion of the intrinsic cardiac cycle.

In particular embodiments, the compressing step can be initiated just before or during the electrical stimulation. The compressing step may be initiated at a time that does not overlap with the T wave portion of a spontaneous intrinsic cardiac cycle.

Other embodiments are directed toward systems for performing chest compression during cardiopulmonary resuscitation (CPR). The systems include: (a) means for electrically stimulating a subject's heart during cardiopulmonary resuscitation; and (b) means for compressing the heart at a selected time proximate to the delivery of the electrical stimulation to avoid compressing the heart during a vulnerable portion of the intrinsic cardiac cycle.

In particular embodiments, the means for compressing can be configured to compress the heart at a time that does not overlap with the T wave portion of a spontaneous intrinsic cardiac cycle. The means for compressing the heart may comprise a mechanically operated device and the system may also include means for automatically controlling the mechanically operated device to apply a mechanical compression responsive to the timing of the electrical stimulation. The device may be an external device configured to reside about a closed chest of the subject or the device may comprise an internal portion that is configured to automatically inflate and deflate to provide a minimally invasive direct cardiac massage.

Other embodiments are directed at methods for performing chest compression during cardiopulmonary resuscitation (CPR). The methods include: sensing a parameter corresponding to a measure of intrinsic spontaneous cardiac activity of a heart in a subject undergoing CPR; and compressing the heart of the subject during a non-vulnerable portion of the intrinsic cardiac based on the sensed parameter.

The compressing step may be initiated at a time that does not overlap with the T wave portion of a spontaneous intrinsic cardiac cycle. The sensing may be carried out using a sensing electrode in communication with an external defibrillator and/or an implantable defibrillator.

The compressing may be carried out by manually compressing the heart. In particular embodiments, an audible alert can be automatically generated when compression is to be initiated to direct a person to initiate manual compression. The manual compression may be a closed chest, minimally invasive massage, or an open chest manual compression. In certain embodiments the compressing may be carried out using a mechanical device and the method may include automatically controlling the device to apply the mechanical compression based on the timing of the intrinsic cardiac cycle as determined by the sensed parameter.

Still other embodiments are directed to systems for assisting in chest compression in a subject having cardiomalfunction. The systems include: (a) at least one cardiac activity sensor in communication with the heart of a subject configured to detect a cardiac activity parameter; (b) a controller in communication with the at least one sensing electrode; and (c) a power supply in communication with the controller, wherein, in operation, the at least one cardiac activity sensor transmits data to the controller regarding a spontaneous intrinsic cardiac cycle of the subject and the controller identifies a favorable time to deliver a chest compression based on the transmitted sensor data.

In particular embodiments, the controller identifies a time that does not overlap with the T wave portion of a spontaneous intrinsic cardiac cycle and may include an audible alert in communication with the controller. The controller can be configured to output an audible alert signal responsive to an identified favorable time to deliver a chest compression to the subject based on the transmitted sensor data. In particular embodiments, the system can include or cooperate with a mechanical device configured to apply chest compression at selected intervals with the controller configured to automatically actively control the timing of the compression applied by the mechanical device (whether an external or internal compression device).

Still other embodiments are directed toward computer program products for timing the delivery of cardiac compression during CPR. The computer program product includes a computer readable storage medium having computer readable program code embodied in the medium. The computer-readable program code includes computer readable program code that determines a favorable time to deliver cardiac compression to a subject to avoid a vulnerable period of a spontaneous intrinsic cardiac cycle.

In certain embodiments, the computer program product can include one or more of: (a) computer readable program code that identifies when electrical stimulation is applied to the subject and that determines the favorable time based on the time that the electrical stimulation is applied; (b) computer readable program code that receives data corresponding to the spontaneous cardiac activity of the subject in substantially real time and that determines the favorable time based on the received data; (c) computer readable program code that outputs an audible alert when a favorable cardiac compression time is determined; and (d) computer readable program code that automatically directs the activation of a mechanical compression device in response to the determined favorable time.

The foregoing and other objects and aspects of the present invention are described in greater detail in the drawings herein and the specification set forth below.

DETAILED DESCRIPTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the claims unless specifically indicated otherwise. Where used, the terms "attached", "connected", "contacting", "coupling" and the like, can mean either directly or indirectly, wirelessly and/or wired, unless stated otherwise. The term "concurrently" means that the operations are carried out substantially simultaneously.

Certain embodiments of the present invention may be used during CPR to inhibit (typically prevent) cardiac tachyarrhythmia, including ventricular fibrillation, and/or to increase cardiac function. The term "CPR" as used herein means delivering cardiac compression, whether manually or mechanically and whether internally via a direct cardiac massage or externally through the chest, at the onset, during, or following a period of cardiac malfunction, typically cardiac arrest. Typically, but not always, CPR may include also ventilating or providing pulmonary assistance, whether manually or with a breathing-assist device to the subject. Subject according to the present invention can be any animal subject, typically a mammalian subject (e.g., human, canine, feline, bovine, caprine, ovine, equine, rodent, porcine, and/or lagomorph), and more typically is a human subject.

The term "mechanical compression device" includes those devices (mechanical and electromechanical) used to compress the cardiac muscle (via the chest or as a direct cardiac massage). The mechanical devices are physical devices, which may be automatically or manually deployed to operate. The automated mechanical compression devices can be used to carry out and/or supplement manual compression using a person's hands or manually operated devices, which can massage the heart (open chest, direct cardiac or heart massage) and/or push down on the closed chest (closed chest massage or "CCM").

As is well known to those of skill in the art, the driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers, and then traveling into the atria and subsequently passing through the AV node and, after a slight delay, into the ventricles.

Figure 1:
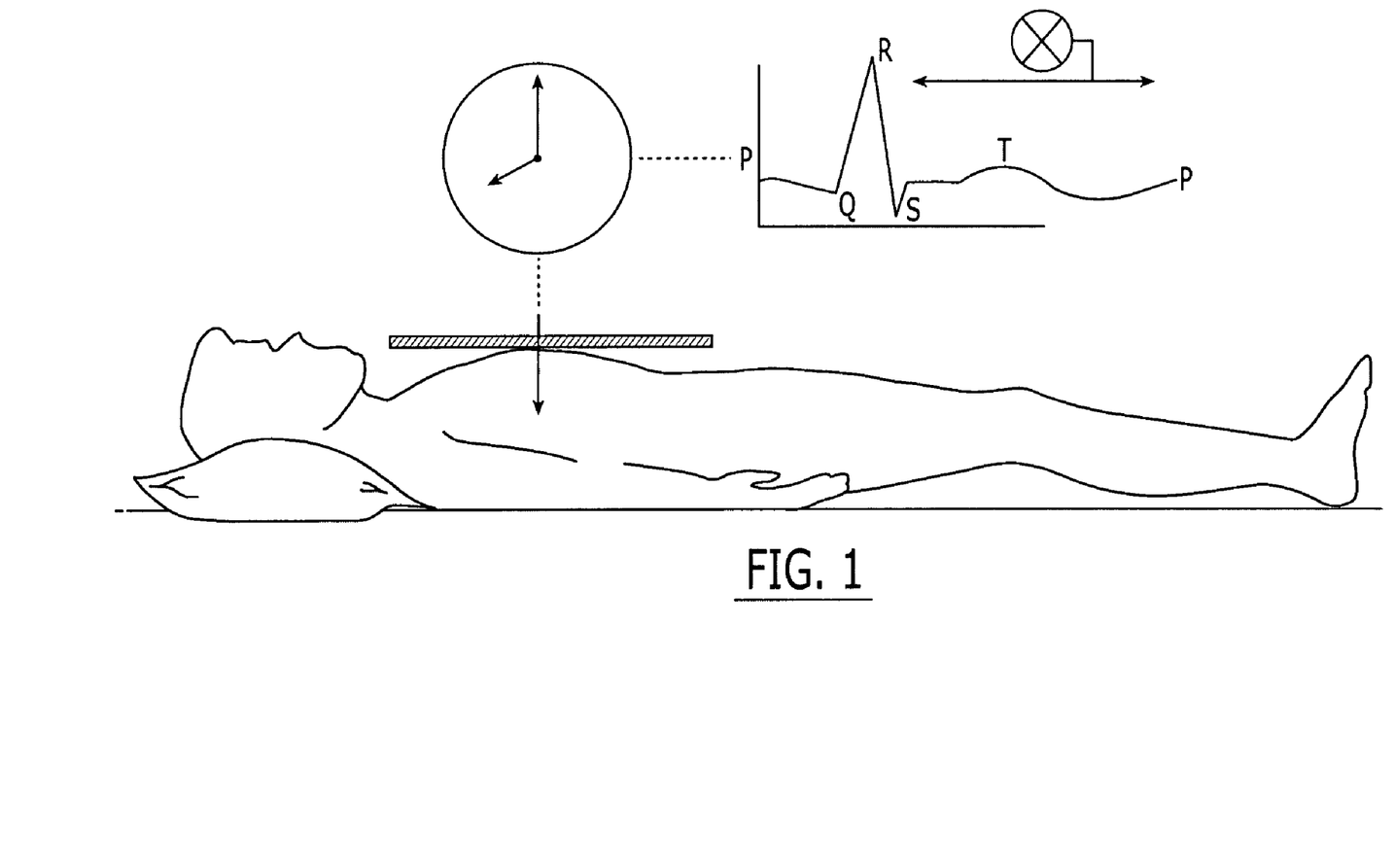
FIG. 1 is a schematic illustration of embodiments of the present invention showing that cardiac compression can be carried out at a desired time during a particular cardiac cycle.

As shown in FIG. 1, an intrinsic cardiac cycle (as measured by an electrocardiogram) is initiated by a P wave, which is normally a small positive wave in the body surface electrocardiogram. The P wave induces depolarization of the atria of the heart. The P wave is followed serially by the Q, R, S and T wave portions of the cardiac cycle. Ventricular fibrillation can occur/recur during CPR. Examination of recordings during past CPR events appears to indicate that many of the noted recurrences of ventricular fibrillation occur during chest compression. This finding suggests that the chest compression during CPR may initiate ventricular fibrillation. It is believed that mechanical stretch of the cardiac fibers during chest compression may cause electrical excitation of these cardiac fibers.

Unless extremely strong, electrical stimulation can typically only induce ventricular fibrillation during a vulnerable period of the cardiac cycle, which occurs during the T wave portion of the electrocardiogram (shown schematically in FIG. 1 as that portion of the cardiac cycle marked with the universal symbol for "do not", i.e., a circle enclosing "X" therein). Conventionally, chest compression during CPR may have been performed independently of and/or without regard to the intrinsic spontaneous cardiac cycle of the subject, suggesting that the noted ventricular fibrillations occurring during/following CPR may have been initiated by compressing the heart non-selectively, thereby causing it to become electrically stimulated during the vulnerable period. Accordingly, as schematically shown in FIG. 1, embodiments of the invention are directed to devices and methods that allow the cardiac compression to be timed to a non-vulnerable period of the cardiac cycle to inhibit the onset of fibrillation and/or increase cardiac function.

Figure 2:
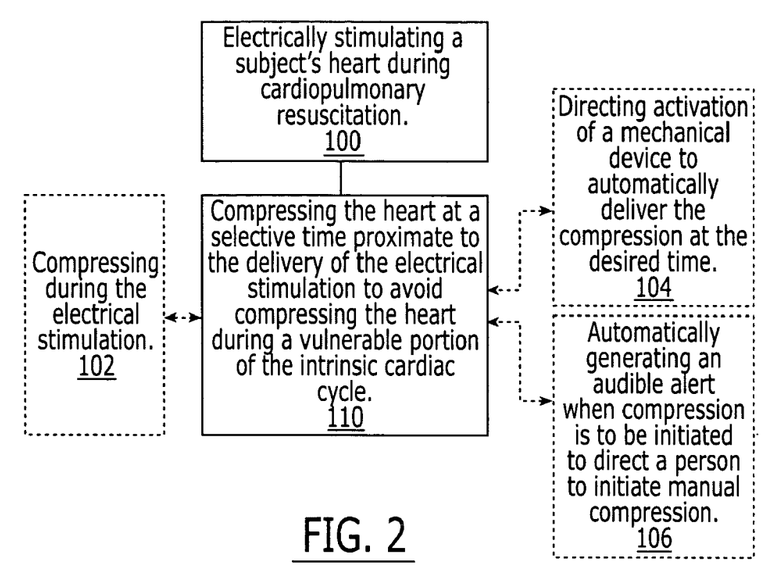
FIG. 2 is a flow chart of operations that can be carried out according to embodiments of the present invention.

As shown in FIG. 2, certain embodiments electrically stimulate the heart to provide or initiate a stimulated cardiac cycle and time the delivery of the cardiac compression based on the timing of the applied electrical stimulus. For a discussion of electrical signals (pacing) that may, in some embodiments, be used to stimulate the heart, see e.g., U.S. patent application Ser. No. 10/238,343, the contents of which are hereby incorporated by reference as if recited in full herein.

Figure 3:
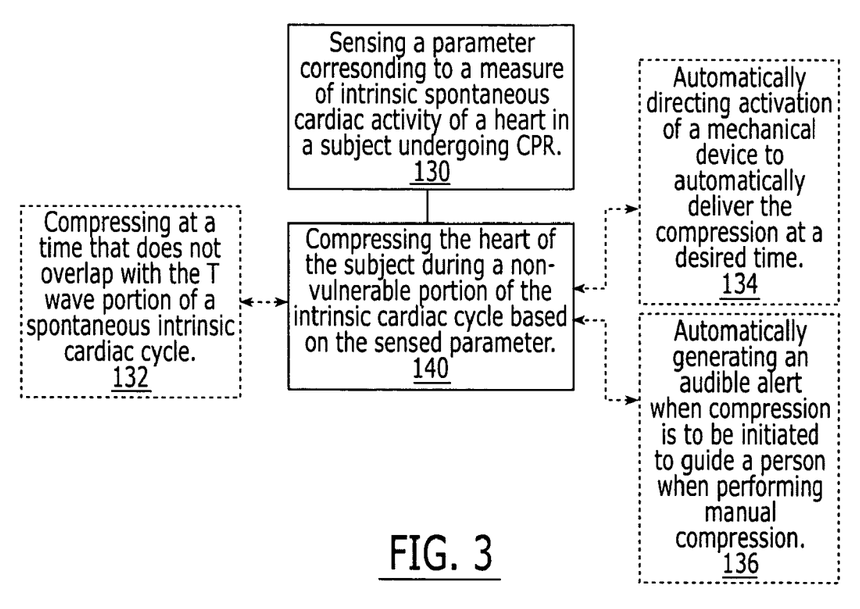
FIG. 3 is a flow chart of alternative operations that can be carried out according to embodiments of the present invention.

In certain embodiments, the compression is timed to be applied during contraction so that compression and contraction are additive, thereby increasing cardiac output. As shown in FIG. 3, other embodiments sense a measure of spontaneous cardiac activity (typically in substantially real-time) and then provide data/feedback to allow the cardiac compression to be applied during a non-vulnerable time or portion of the cardiac cycle. Combinations of the above may also be used as appropriate.

Referring now to FIG. 2, a subject's heart can be electrically stimulated during cardiopulmonary resuscitation (block 100). The heart can be compressed at a selective time proximate to the delivery of the electrical stimulation to avoid compressing the heart during a vulnerable portion of the intrinsic cardiac cycle (block 110). The compressing may be initiated and/or carried out just before, during or just after the electrical stimulation. As shown, the compressing may be carried out during or overlapping with the electrical stimulation (block 102). In certain embodiments, the compressing may be carried out within about 1 second before or after and more typically within about 0.5 seconds before or after the electrical stimulation. The activation of a mechanical compression device can be controlled to automatically deliver the compression at a desired time (block 104). In addition, or alternatively, an alert can be automatically generated when a favorable cardiac compression time or opportunity is determined to guide a user applying manual compression as to the appropriate timing of same (block 106). The alert may be an audible message, a sound or a combination of same. In addition, or alternatively, visual tactile signals can also be used to prod a user as to when to deliver the compression. The visual signal may be provided by a light (in color (green/red), blinking lights and/or a screen display). The tactile signal may be a force applied by a wrist band or other tactile feedback member to indicate initiate and/or stop compression. For example, in operation, a voice message can be transmitted stating "Apply Cardiocompression Now". The audible alert may also note when to stop the cardiocompression, such as "Stop Cardiocompression Now". Different audible signals (beeps, buzzers, sirens, chimes and the like) may be used to help guide the user in this action such as by using a first sound during a suitable compression period and a different sound when compression should be stopped and/or an increasing decibel output as time becomes more critical (as the cardiac cycle approaches a more vulnerable stage).

In other embodiments as shown in FIG. 3, a parameter corresponding to a measure of intrinsic spontaneous cardiac activity of a heart in a subject undergoing CPR can be sensed (block 130). The heart can be compressed at a selective time proximate to the delivery of the electrical stimulation during a non-vulnerable portion of the intrinsic cardiac cycle based on the data provided by the sensed parameter (block 140). As before, the compression can be carried out at a time that does not overlap with the T wave portion of a spontaneous intrinsic cardiac cycle (block 132). The sensed data can be used to automatically direct or control the activation of a mechanical device to automatically deliver the compression at a desired selective time (block 134). An alert (typically comprising an audible signal) can be automatically generated to help guide a person as to when compression should be applied when a person is manually performing the compression (block 136).

The cardiac activity parameter can be one or more parameters associated with the electrical activity of the heart such as provided by data from an electrocardiogram signal. In addition, or alternatively, a blood pressure measurement, thoracic impedance or other suitable measure of cardiac activity can be used. The cardiac activity parameter can be obtained from a cardiac activity sensor that may be positioned on or in the subject. In certain embodiments, the sensor can include a skin or surface mountable electrical activity electrode sensor(s) and/or an implanted sensor (typically integrated in an implantable defibrillator).

Figure 4A:
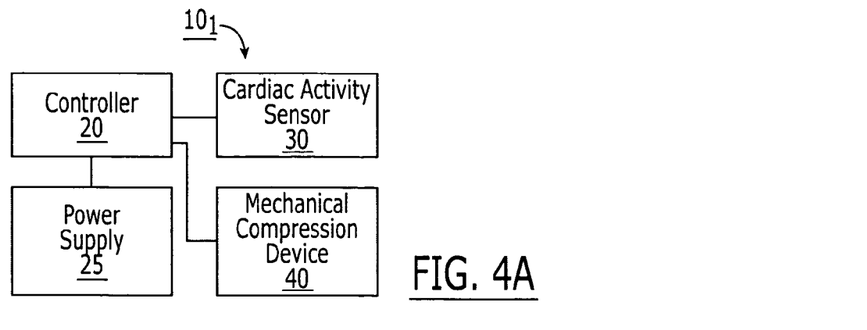
FIG. 4A is a block diagram of a system according to embodiments of the present invention.
Figure 4B:
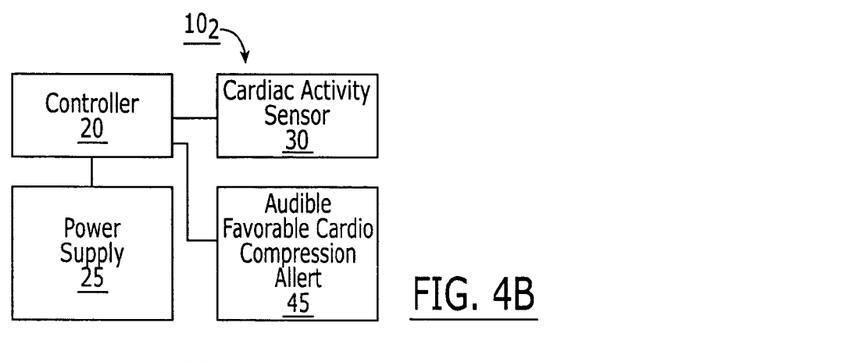
FIG. 4B is a block diagram of a system according to other embodiments of the present invention.
Figure 5A:
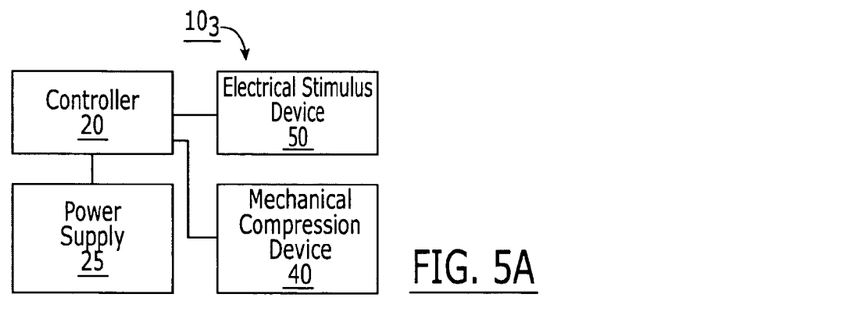
FIG. 5A is a block diagram of a system according to additional embodiments of the present invention.
Figure 5B:
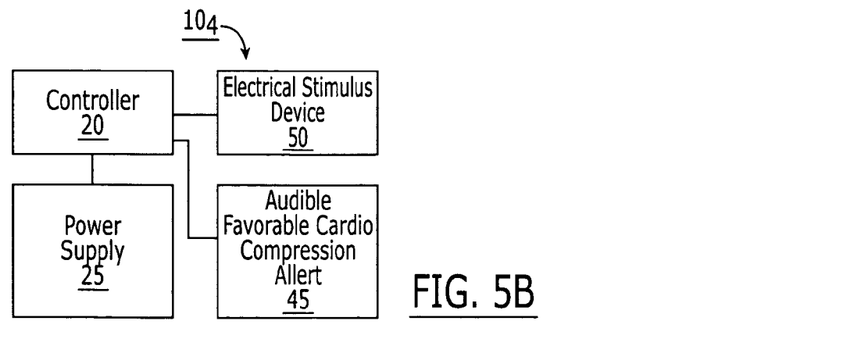
FIG. 5B is a block diagram of a system according to further embodiments of the present invention.

FIGS. 4A and 4B illustrate cardiocompression assist systems that may be used to carry out operations illustrated in FIG. 3 according to certain embodiments of the present invention. FIGS. 5A and 5B illustrate cardiocompression assist systems that can be used to carry out operations illustrated in FIG. 2. Each of the cardiocompression systems can be referred to generically by reference number 10, and individually by the subscript shown, $10_1$, $10_2$, $10_3$, $10_4$. As shown, each system 10 can include or be in communication with a controller 20 and power supply 25.

FIGS. 4A and 4B illustrate that the system can include or cooperate with a cardiac activity sensor 30. The system $10_1$ shown in FIG. 4A includes a controller 20 that can direct the activation of an automatic or semi-automatic mechanical compression device 40 based on the substantially real time data on the cardiac activity provided by the sensor 30. The system $10_1$ can include the mechanical device 40 or be configured to cooperate with an existing device 40. As shown in FIG. 4B, the system $10_2$ can include and/or be in communication with an alert device or component 45. The controller 20 can direct the output of a favorable compression alert based on the data provided by the cardiac activity sensor 30 to help guide the timing of manually delivered compression. The alert 45 may comprise an audible favorable cardiocompression alert as shown, and/or other alert signals such as but not limited to, tactile and visual alert signals as discussed above. Examples of suitable mechanical devices will be discussed further below.

FIGS. 5A and 5B illustrate systems $10_3$ and $10_4$ can include and/or be in communication with an electrical stimulus device 50 capable of stimulating cardiac activity. The system $10_3$ shown in FIG. 5A includes and/or is in communication with a (automatic or semi-automatic) mechanical compression device 40. An example of an electrical stimulus device 50 is an external and/or implantable defibrillator configured to apply an electrical shock to the heart of the subject. An electrode(s) in communication with the stimulus device may be integrated with an external compression device, such as an inflatable vest and/or a thumper external or other device as will be discussed further below.

As shown in FIG. 5B, the system $10_4$ can also include and/or be in communication with an alert device or component 45. The controller 20 can direct the output of a favorable compression alert based on the data provided by the timing of the stimulus to help guide the timing of manually delivered compression. The alert 45 may comprise an audible favorable cardiocompression alert as shown, and/or other alert signals such as, but not limited to, tactile and visual alert signals as discussed above. Examples of suitable mechanical devices will be discussed further below. The cardiocompression system 10 may also include combinations of the features shown in systems $10_1$, $10_2$, $10_3$, $10_4$. For example, the system 10 can include or be in communication with both a cardiac activity sensor 30 and an electrical stimulus device 50.

Figure 6:
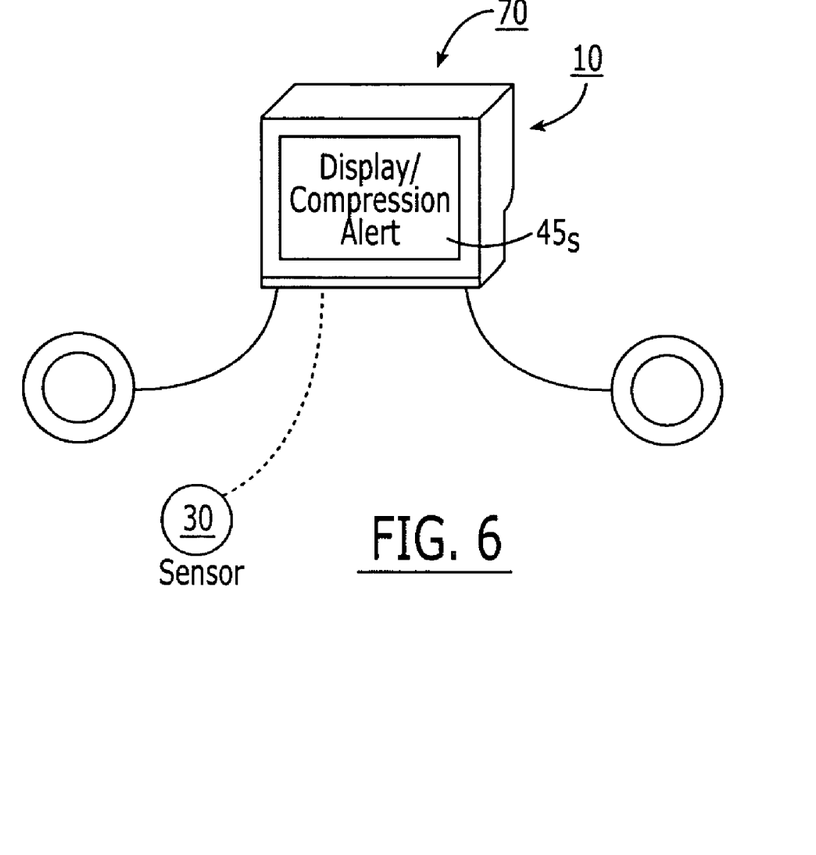
FIG. 6 is a schematic illustration of an external defibrillator with an integrated cardiac activity sensor and controller to time/identify a favorable compression period according to embodiments of the present invention.

The cardiocompression system 10 may be incorporated into existing patient monitoring or therapeutic devices or configured as a stand-alone unit that provides the timing of cardiac compression during CPR. For example, as shown in FIG. 6, an external defibrillator 70 can be configured to provide the compression alert signal 45s whether based on sensing cardiac activity (FIG. 3) or based on the timing of the delivery of the stimulus. Thus, as shown, the device 70 may optionally include a cardiac activity sensor 30. The sensor 30 can be deactivated or electrically insulated during application of a stimulus shock as desired. If manual compression is to be used proximate to delivery of electrical stimulation (particularly externally applied) a person should use insulating gloves to inhibit the person from receiving an undue electrical shock.

Figure 7:
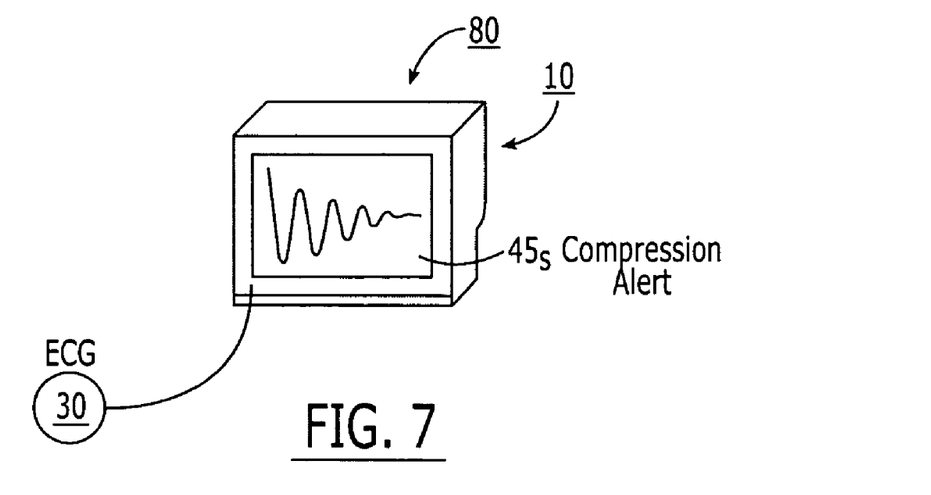
FIG. 7 is a schematic illustration of an ECG device with an integrated favorable cardiac compression alert module according to embodiments of the present invention.

FIG. 7 illustrates that an electrocardiographic (ECG) machine 80 can be configured to incorporate cardiocompression timing to provide the cardiocompression alert signal 45s and/or direct the activation of mechanical devices 40. The electrodes of the ECG may be suitable to provide the sensed cardiac activity.

Figure 8:
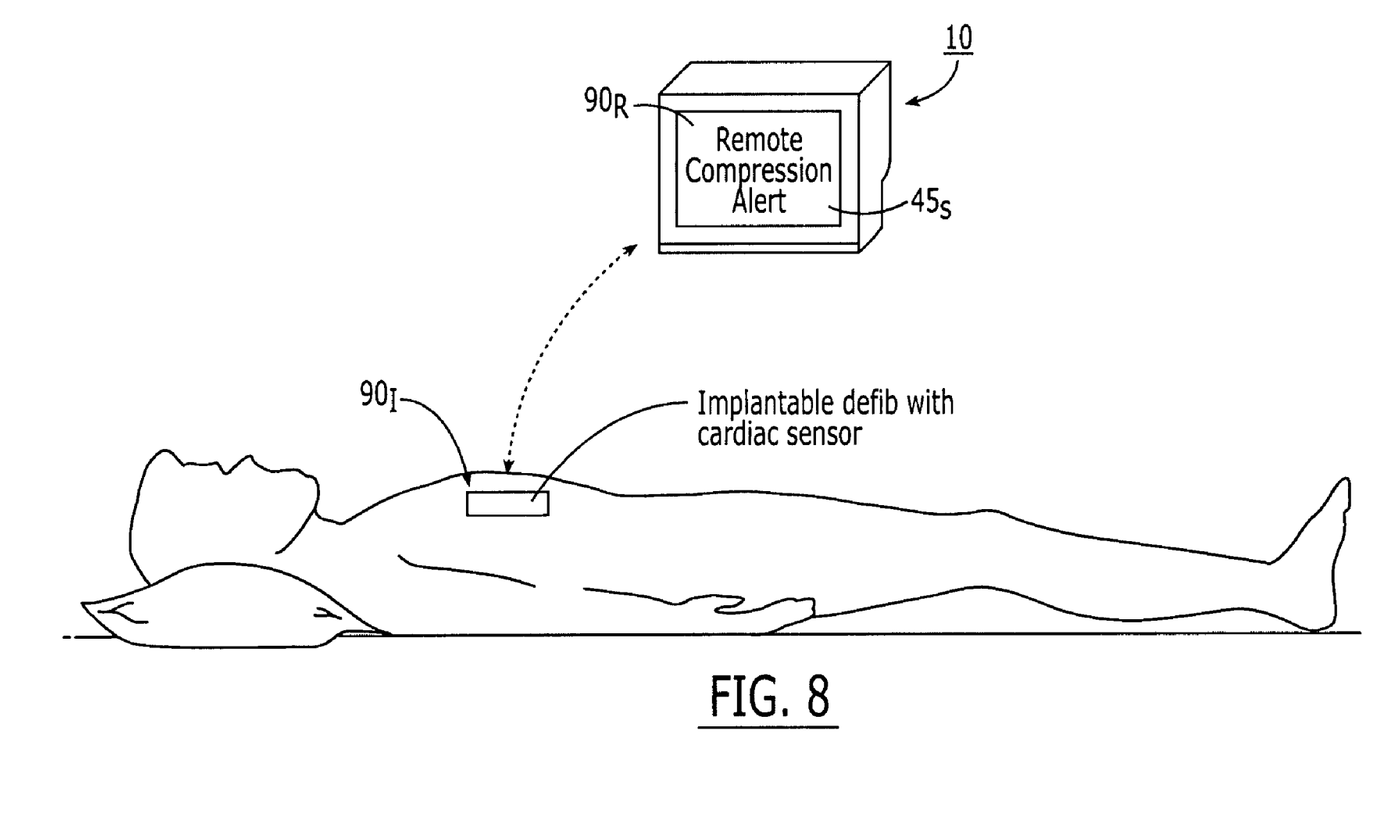
FIG. 8 is a schematic illustration of an implantable defibrillator in communication with a remote favorable cardiac compression alert device according to embodiments of the present invention.

FIG. 8 illustrates a system 10 which is configured with a remote housing 90R that can be configured to wirelessly communicate with an implanted defibrillator/pacemaker 90I. The remote housing 90R can include the controller 20 that receives data transmitted from the implanted defibrillator/pacemaker 90I to generate the compression alert signal 45s and/or direct the activation of the mechanical device 40 (FIGS. 4A, 5A). The implanted device 90I can be configured to provide the cardiac activity data and/or the electrical stimulus.

Figure 9:
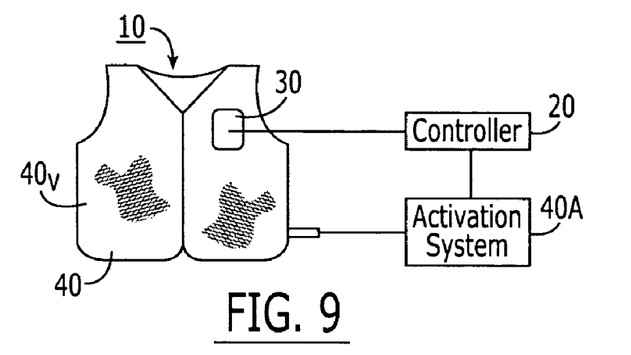
FIG. 9 is a schematic illustration of a mechanical compression device in communication with a favorable cardiac compression timing and control system according to embodiments of the present invention.

FIG. 9 illustrates an example of system 10 in communication with a mechanical device 40 configured to provide compression at a selective time to inhibit compression during a vulnerable period of the cardiac cycle. As shown, the device 40 is an inflatable vest 40v having a fluid inflation source and activation system (typically pneumatic) configured to inflate and deflate to apply chest compression. The system 10 can include a sensor 30 that is in communication with controller 20 as shown and/or employ an electrical stimulus device as described above. In operation, the controller 20 can direct the activation system 40A to selectively time the delivery of the compression to avoid a vulnerable portion of the cardiac cycle. In certain embodiments, the system 10 can be configured to activate the vest 40v to rapidly compress and apply pressure during a non-vulnerable time and to even more rapidly stop (i.e., exhaust air or fluid and deflate within or less than about 3 ms, and typically less than about 1 ms) the compression if cardiac activity indicates a vulnerable period. In addition, in certain embodiments, timing of compression provided by leg compression devices, where used, may also be controlled. An example of an inflatable vest is described in U.S. Pat. No. 6,179,793, the contents of which are hereby incorporated by reference as if recited in full herein. Other inflatable bladder chest compressors are described in U.S. Pat. Nos. 2,071,215, 4,424,806 and 4,928,674, the contents of which are also incorporated by reference as if recited in full herein. In some cases, a stiff outer shell or biasing cuff surrounds the bladder so that when the bladder is periodically inflated, the patient's chest is compressed, causing expiration and inspiration. Still other cardiac assist devices employing inflatable cuffs and other mechanisms are described in U.S. Pat. Nos. 5,256,132; 5,169,381; 4,731,076; 4,690,134; 4,536,893; 4,192,293; 4,048,990; 3,613,672; 3,455,298; and 2,826,193. The contents of these patents are also incorporated by reference as if recited in full herein.

In certain embodiments, internal automated or semi-automated suitable mechanical devices 50 that are configured to provide minimally invasive direct cardiac massage (MIDCM) can be controlled according to embodiments of the present invention. Examples of MIDCM devices are described in U.S. Pat. Nos. 6,200,280, 6,503,265, and 6,059,750, the contents of which are hereby incorporated by reference as if recited in full herein. Other direct massage devices are described in U.S. Pat. Nos. 5,582,580, 5,571,074, 5,484,391 5,683,364, 5,466,221 and 5,385,528, the contents of which are hereby incorporated by reference as if recited in full herein. Dissectors employing inflatable components are described in U.S. Pat. Nos. 5,730,756; 5,730,748; 5,716,325; 5,707,390; 5,702,417; 5,702,416; 5,694,951; 5,690,668; 5,685,826; 5,667,520; 5,667,479; 5,653,726; 5,624,381; 5,618,287; 5,607,443; 5,601,590; 5,601,589; 5,601,581; 5,593,418; 5,573,517; 5,540,711; 5,514,153; and 5,496,345. The contents of these patents are also incorporated by reference as if recited in full herein.

Examples of manual mechanical devices can be found in U.S. Pat. No. 3,219,031, U.S. Pat. No. 3,509,899, U.S. Pat. No. 3,896,797, and U.S. Pat. No. 4,397,306. Each of these patents describe devices which use a reciprocating plunger to compress a victim's chest along with a means of ventilating the victim, such as a source of pressurized oxygen or a squeeze bag. Certain hand held devices have been employed to serve both these functions. Indeed, the popular media have reported on the use of a suction cup plunger, often referred to as a "plumber's helper", having been used to provide enhanced CPR. A past study determined that where cardiac support is provided by rhythmic chest compressions, cardiac output could be significantly improved by alternating chest compressions with chest decompressions. In this study, the chest was compressed and decompressed using a rubber plunger which alternately applied pressure and suction to the patient's chest. See Cohen, T. J., et al., "Active Compression-Decompression: A New Method of Cardiopulmonary Resuscitation", J. Am. Med. Assoc. Vol. 267, No. 21, pp. 2916-23, 1992. This technique is known as active compression-decompression CPR ("ACD CPR"). ACD CPR is reported as being significantly more effective than conventional "compression-only" CPR. It provides both perfusion and ventilation, and can resuscitate some patients where conventional CPR and defibrillation fail. Devices capable of being used to perform ACD CPR are also described in U.S. Pat. No. 5,295,481 and European Patent Application No. 92303367.4 (Publication No. 0 509 773 A1). Each of these patents shows a device which includes a suction cup and handle. In each case, the aid giver would grab the handle and alternately press down and then pull up. The downward pressure would force air out of the lungs and blood out of the heart, while the pulling up on the handle would cause the suction cup to draw the chest upwardly to pull air into the lungs and blood into the heart. Another example of an external device 50 for providing ACR using an external beam is described in U.S. Pat. No. 5,630,789, the contents of which is incorporated by reference as if recited in full herein.

Figure 10:
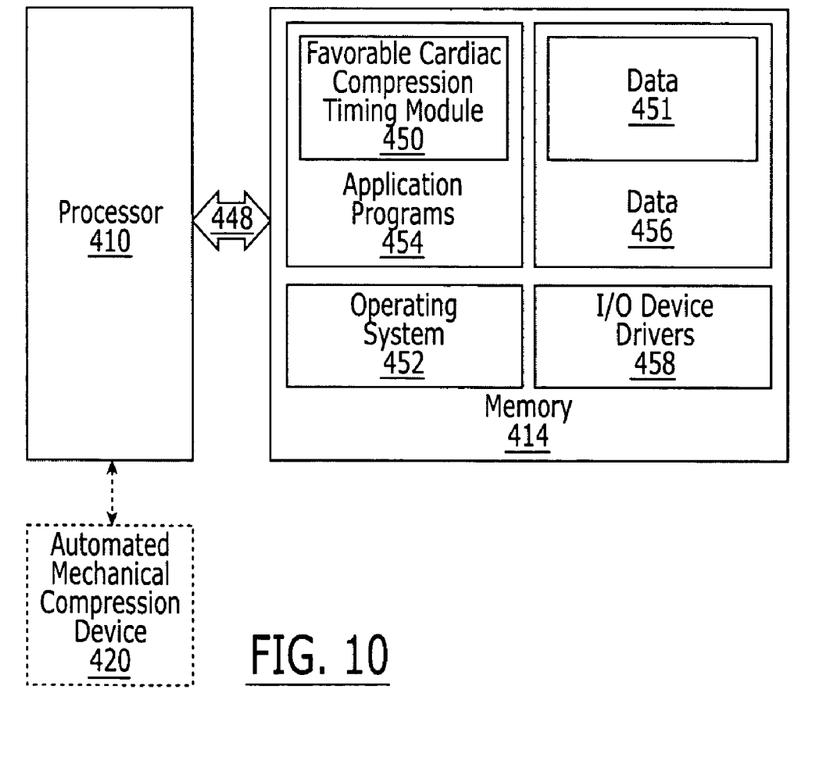
FIG. 10 is a block diagram of a data processing system according to embodiments of the present invention.

FIG. 10 is a block diagram of exemplary embodiments of data processing systems that illustrates systems, methods, and computer program products in accordance with embodiments of the present invention. The processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system 405. The memory 414 can include, but is not limited to, the following types of devices: cache, ROM, PROM, EPROM, EEPROM, flash memory, SRAM, and DRAM.

As shown in FIG. 10, the memory 414 may include several categories of software and data used in the data processing system 405: the operating system 452; the application programs 454; the input/output (I/O) device drivers 458; the Cardiocompression Timing Module 450; and the data 456.

The data 456 may include substantially real-time sensed cardiac activity 451 and/or the timing of an electrical stimulus. The processor 410 can be in communication with an automated mechanical compression device 40 and/or stimulus device 50. As will be appreciated by those of skill in the art, the operating system 452 may be any operating system suitable for use with a data processing system, such as OS/2, AIX, DOS, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components and/or the device 420. The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the CarioCompression Module 450 being an application program in FIG. 10, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system 405. Thus, the present invention should not be construed as limited to the configuration of FIG. 10, which is intended to encompass any configuration capable of carrying out the operations described herein.

The I/O data port can be used to transfer information between the data processing system 405 and the closure attachment mechanism (such as for chubbed linked product) 420 or another computer system or a network (e.g., the Internet) or to other devices controlled by the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 10 but is intended to encompass any configuration capable of carrying out the operations described herein.

The flowcharts and block diagrams of certain of the figures herein illustrate the architecture, functionality, and operation of possible implementations of selective implementation of single and dual clip closure means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

In summary, certain embodiments of the present invention provide devices, methods and/or computer program products that can allow cardiac compression to be selectively delivered during cardiopulmonary resuscitation and to be timed to a desired portion of an intrinsic spontaneous cardiac cycle and/or an electrical stimulus event to inhibit (typically prevent) arrhythmias and/or improve cardiac function.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for performing chest compression during cardiopulmonary resuscitation (CPR), comprising;
   sensing a parameter corresponding to a measure of intrinsic spontaneous cardiac activity of a heart in a subject undergoing CPR;
   identifying a vulnerable portion of an intrinsic spontaneous cardiac cycle of the subject; and
   compressing the heart of the subject during a non-vulnerable portion of the spontaneous intrinsic cardiac cycle that avoids a vulnerable period of the spontaneous intrinsic cardiac cycle based on the identifying step thereby inhibiting reinduction of fibrillation and/or improving cardiac function.

2. A method according to claim 1, wherein the sensing is carried out in substantially real-time.

3. A method according to claim 1, wherein the compressing step is initiated at a time that does not overlap with a T wave portion of the spontaneous intrinsic cardiac cycle.

4. A method according to claim 1, wherein the sensing step is carried out using a sensing electrode in communication with an external defibrillator.

5. A method according to claim 1, wherein the sensing step is carried out using an internal sensing electrode in communication with an implantable defibrillator.

6. A method according to claim 1, wherein compressing the heart comprises manually compressing the heart.

7. A method according to claim 6, further comprising automatically generating an audible alert when compression is to be initiated to direct a person to initiate manual compression.

8. A method according to claim 6, wherein the manual compression is a closed chest manual compression.

9. A method according to claim 6, wherein the manual compression is an internal chest compression.

10. A method according to claim 6, wherein the manual compression is an open chest compression.

11. A method according to claim 1, wherein compressing the heart comprises mechanically compressing the heart using a compression device.

12. A method according to claim 1, further comprising automatically controlling the device to apply the mechanical compression based on the timing of the intrinsic cardiac cycle as determined by the sensed parameter.

13. A method according to claim 12, wherein the device is an external device residing on a closed chest of the subject.

14. A method according to claim 13, wherein the external device comprises an inflatable vest configured to compress the chest.

15. A method according to claim 12, wherein the device comprises an internal portion that automatically inflates and deflates to provide a minimally invasive direct cardiac massage.

16. A method according to claim 1, further comprising audibly alerting when to start the compressing and when to stop the compressing based on the identifying step.

17. A method according to claim 1, further comprising applying an electrical stimulation within about 1 second of the compressing step.

18. A system for assisting in chest compression in a subject having cardiomalfunction, comprising:
   at least one cardiac activity sensor in communication with the heart of a subject configured to detect a cardiac activity parameter; and
   a controller in communication with the at least one cardiac activity sensor, wherein, in operation, the at least one cardiac activity sensor transmits data to the controller regarding a spontaneous intrinsic cardiac cycle of the subject and the controller identifies a favorable time to deliver a chest compression based on the transmitted sensor data to avoid a vulnerable portion of the spontaneous intrinsic cardiac cycle, wherein the controller identifies a time that does not overlap with the T wave portion of the spontaneous intrinsic cardiac cycle.

19. A system according to claim 18, further comprising a mechanical device configured to apply chest compression at selected intervals, the controller configured to automatically actively control the timing of the compression applied by the mechanical device.

20. A system according to claim 19, wherein the mechanical device is an external compression device.

21. A system according to claim 19, wherein the mechanical device comprises an internal compression device.

22. A system according to claim 18, wherein the the controller is further configured to audibly generate when to start compression and when to stop compression to avoid a vulnerable portion of a spontaneous intrinsic cardiac cycle of the subject.

23. A system according to claim 18, further comprising an audio alert in communication with the controller wherein, in operation, the audio alert is configured to signal when to start compression and when to stop compression to avoid the vulnerable portion of the spontaneous intrinsic cardiac cycle.

24. A system according to claim 18, further comprising an electrical stimulation source in communication with the controller, wherein the system is configured to apply electrical stimulation to the chest of the subject within about 1 second of the compression.

25. A system for assisting in chest compression in a subject having cardiomalfunction, comprising:
   at least one cardiac activity sensor in communication with the heart of a subject configured to detect a cardiac activity parameter; and
   a controller in communication with the at least one cardiac activity sensor, wherein, in operation, the at least one cardiac activity sensor transmits data to the controller regarding a spontaneous intrinsic cardiac cycle of the subject and the controller identifies a favorable time to deliver a chest compression based on the transmitted sensor data to avoid a vulnerable portion of the spontaneous intrinsic cardiac cycle, further comprising an audible alert in communication with the controller, the controller configured to output an audible alert signal responsive to an identified favorable time to deliver a chest compression to the subject based on the transmitted sensor data.

26. A system according to claim 25, further comprising a power supply in communication with the controller and a display configured to display a spontaneous intrinsic cycle and visually indicate a favorable time to deliver a chest compression based on the transmitted sensor data.

27. A computer program product for timing the delivery of cardiac compression during CPR, the computer program product comprising:
   a computer readable storage medium having computer readable program code embodied in said medium, said computer-readable program code comprising:
   computer readable program code that identifies a vulnerable portion of an intrinsic spontaneous cardiac cycle of the subject; and
   computer readable program code that determines a favorable time to deliver cardiac compression to a subject to avoid a vulnerable period of the spontaneous intrinsic cardiac cycle.

28. A computer program product according to claim 27, further comprising computer readable program code that identifies when electrical stimulation is applied to the subject, wherein the computer readable program code that determines the favorable time is based on the time that the electrical stimulation is applied.

29. A computer program product according to claim 27, further comprising computer readable program code that receives data corresponding to the spontaneous cardiac activity of the subject in substantially real time, wherein the computer readable program code that determines the favorable time is based on the identified vulnerable portion of the cardiac cycle and the received data.

30. A computer program product according to claim 27, further comprising computer readable program code that outputs an audible alert when a favorable cardiac compression time is determined.

31. A computer program product according to claim 30, further comprising computer readable program code that automatically directs the activation of a mechanical compression device in response to the determined favorable time.

32. A computer program product according to claim 30, further comprising computer readable program code that outputs an audible alert when to stop compression to avoid an unfavorable cardiac compression time.

* * * * *

UNITED STATES PATENT AND TRADEMARK OFFICE
CERTIFICATE OF CORRECTION

PATENT NO.          : 7,734,344 B2                                        Page 1 of 1
APPLICATION NO. : 10/727123
DATED                  : June 8, 2010
INVENTOR(S)       : Ideker et al.

It is certified that error appears in the above-identified patent and that said Letters Patent is hereby corrected as shown below:

Title Page:
Item (56) References Cited, U.S. Patent Documents:
　　　　　　　　　　　Please include -- 2,826,193   11/1965   Rentsch, Jr. --

Signed and Sealed this

Twenty-third Day of November, 2010

David J. Kappos
*Director of the United States Patent and Trademark Office*